(12) United States Patent
Li et al.

(10) Patent No.: US 10,989,702 B2
(45) Date of Patent: Apr. 27, 2021

(54) LABORATORY TRACER EXPERIMENT SYSTEM FOR MEDIUM CHARACTERISTIC INVERSION OF KARST CONDUIT

(71) Applicant: SHANDONG UNIVERSITY, Shandong (CN)

(72) Inventors: Shucai Li, Jinan (CN); Xintong Wang, Jinan (CN); Zhenhao Xu, Jinan (CN); Peng Lin, Jinan (CN); Dongdong Pan, Jinan (CN); Xin Huang, Jinan (CN); Bin Gao, Jinan (CN); Wenyang Wang, Jinan (CN)

(73) Assignee: SHANDONG UNIVERSITY, Jinan (CN)

( * ) Notice: Subject to any disclaimer, the term of this patent is extended or adjusted under 35 U.S.C. 154(b) by 196 days.

(21) Appl. No.: 16/466,787

(22) PCT Filed: Jul. 27, 2018

(86) PCT No.: PCT/CN2018/097475
§ 371 (c)(1),
(2) Date: Jun. 5, 2019

(87) PCT Pub. No.: WO2020/000557
PCT Pub. Date: Jan. 2, 2020

(65) Prior Publication Data
US 2020/0400644 A1    Dec. 24, 2020

(30) Foreign Application Priority Data
Jun. 25, 2018  (CN) .......................... 201810659975.3

(51) Int. Cl.
*G06G 7/50*    (2006.01)
*G01N 33/24*    (2006.01)
(Continued)

(52) U.S. Cl.
CPC ............ *G01N 33/246* (2013.01); *G09B 23/40* (2013.01); *G09B 25/06* (2013.01); *G09B 25/08* (2013.01)

(58) Field of Classification Search
CPC ....... G01N 33/246; G09B 23/40; G09B 25/06; G09B 25/08
See application file for complete search history.

(56) References Cited

U.S. PATENT DOCUMENTS

| 5,807,697 A | 9/1998 | Strong-Gunderson et al. |
| 2011/0295581 A1* | 12/2011 | Montaron ............... E21B 49/00 703/10 |

FOREIGN PATENT DOCUMENTS

| CN | 103335989 A | 10/2013 |
| CN | 104282214 A | 1/2015 |

(Continued)

OTHER PUBLICATIONS

Lauber et al. (Use of artificial and natural tracers to assess groundwater transit-time distribution and flow systems in a high-alpine karst system, 180 pages) (Year: 2014).*

(Continued)

*Primary Examiner* — Andre Pierre Louis
(74) *Attorney, Agent, or Firm* — Oliff PLC

(57) ABSTRACT

A laboratory tracer experiment system based on karst conduit medium characteristic inversion, having: a assembly model system of the karst conduit medium; a test bed, configured to support the assembly model system of the karst conduit medium; a water supply system connected to the assembly model system of the karst conduit medium to supply water to the assembly model system of the karst conduit medium; a full-automatic control system for tracer adding connected to the assembly model system of the karst conduit medium to add a prepared tracer solution into the assembly model system of the karst conduit medium; a (Continued)

real-time wireless monitoring system of fluorescent tracer; and a central control system for controlling the full-automatic control system for tracer adding, the water supply system, the real-time wireless monitoring system of fluorescent tracer and the high-definition camera recording system to communicate with the central control system.

10 Claims, 3 Drawing Sheets

(51) Int. Cl.
*G09B 23/40* (2006.01)
*G06G 7/48* (2006.01)
*G09B 25/06* (2006.01)
*G09B 25/08* (2006.01)

(56) References Cited

FOREIGN PATENT DOCUMENTS

| CN | 108020489 A | 5/2018 |
| CN | 108169413 A | 6/2018 |

OTHER PUBLICATIONS

Li (A laboratory simulation of solute transport and retention in a karst aquifer, 2011 pages) (Year: 2004).*
Apr. 2, 2019 International Search Report issued in International Patent Application No. PCT/CN2018/097475.

* cited by examiner

LABORATORY TRACER EXPERIMENT SYSTEM FOR MEDIUM CHARACTERISTIC INVERSION OF KARST CONDUIT

FIELD OF THE INVENTION

The present invention relates to the technical fields of hydrogeology, hydrology and water resource engineering, groundwater and science engineering, environmental science and engineering, water resource and environmental engineering, engineering geology and the like, in particular to a laboratory tracer experiment system based on karst conduit medium characteristic inversion.

BACKGROUND OF THE INVENTION

There are a large number of karst strata in the southwest of China, and many karst landforms such as underground rivers, conduits, ponors, caves and fluid bowls are formed due to extremely complex geological conditions. At present, with the rapid development of economic construction, a large number of major foundation engineering such as water conservancy and hydropower projects, railway and highway traffic engineering are being transferred to these karst areas. Because underground rivers and conduits under the earth surface are unlikely to discover, there are severe security risks during construction of underground projects. Therefore, in order to ensure the safety of engineering construction, it is imperative to find out the development degree and structural conditions of karst conduit media in the southwest. The karst groundwater tracer experiment is a hydrogeological experiment that can accurately detect and analyze karst conduit media, and is one of the important means for studying groundwater transport, pollution sources and karst conduit forms. The tracer technology can accurately and economically determine hydrological parameters of groundwater flow, and detect types and structural characteristics of the underground karst conduit media in a short time according to the characteristics of received concentration curves.

At present, scholars at home and abroad have carried out a series of field tracer monitoring experiments onto reservoirs, dams, oil fields, coal-bed methane wells and other projects, and explored recharge sources and ways of karst groundwater on project sites, but no relatively systematic laboratory tracer experiment has been carried out, there's a lack of devices and methods related to tracer technology analysis on karst conduit media, and feasible technical means for laboratory tracer exploration experiments have not been proposed. In conclusion, it is necessary to develop a laboratory tracer experiment system based on karst conduit medium characteristic inversion to solve the above problems.

SUMMARY OF THE INVENTION

In order to overcome the deficiencies of the above technologies, the present invention provides a laboratory tracer experiment system based on karst conduit medium characteristic inversion, which is easy to operate and convenient to monitor.

In order to achieve the above objectives, the present invention adopts the following technical solution:
A laboratory tracer experiment system based on karst conduit medium characteristic inversion consists of a assembly model system of the karst conduit medium, a test bed, a water supply system, a full-automatic control system for tracer adding, a real-time wireless monitoring system of fluorescent tracer, a central control system and a high-definition camera recording system;

the assembly model system of the karst conduit medium consists of a series of conceptual model of karst conduits of designed sizes and types, and is configured to simulate different types of underground karst media; flow rate measurement and tracer adding are carried out at an inlet of each conduit, and real-time data acquisition and monitoring are carried out at an outlet to obtain tracer curve characteristics of different karst medium structures;

the test bed is configured to support the assembly model system of the karst conduit medium;

the water supply system is connected to the assembly model system of the karst conduit medium to supply water to the assembly model system of the karst conduit medium;

the full-automatic control system for tracer adding is connected to the assembly model system of the karst conduit medium to add a prepared tracer solution into the assembly model system of the karst conduit medium;

the real-time wireless monitoring system of fluorescent tracer is configured to monitor the concentration of a fluorescent tracer and the flow rate in real time, and implement remote wireless transmission of data;

the high-definition camera recording system is configured to record and shoot the whole transport process of the fluorescent tracer in the conduit, and transmit images and videos in real time to the central control system wirelessly, and the images and videos and the collected tracer concentration and flow rate are visually displayed on the display screen to provide basis and help for processing and analyzing late data;

the central control system controls the full-automatic control system for tracer adding, the water supply system, the real-time wireless monitoring system of fluorescent tracer and the high-definition camera recording system to communicate with the central control system.

Further, the conduit model is made of a transparent material, and can be used for visually observing the change in tracer concentration during a tracer experiment; an opening connected to the full-automatic control system for tracer adding is disposed at a position of the conduit model near the inlet, an opening connected to the real-time wireless monitoring system of fluorescent tracer is disposed near the outlet, and the openings are sealed by seal rings to prevent leakage of liquid during the experiment. Further, the test bed consists of a bed base and support frames, and drainage channels are disposed in the middle of and on four sides of the bed base to discharge excess water in the experiment to sewers; two slide rails are disposed on two sides of the middle drainage channel, a plurality of height adjustable support frames is mounted on the two slide rails, and the assembly model system of the karst conduit medium is mounted on the support frames.

Further, the full-automatic control system for tracer adding consists of a water supply device, an integrated three-chamber-combined device, a central control system and an online real-time monitoring device;

the integrated three-chamber-combined device consists of a premixing chamber, a mixing chamber and a storage chamber which are sequentially connected;

the premixing chamber is used for storing dry powder of three tracers, i.e., rhodamine, fluorescein sodium and Tinopal, a weighing device is disposed at the bottom of the premixing chamber, and the weighing device is configured to detect the weight of the dry tracer powder and send detected signals to the central control system; the central control system controls the weight of the dry tracer powder entering the mixing chamber;

the mixing chamber is used for preparation of a tracer solvent, and the water supply device supplies water to the mixing chamber; the mixing chamber consists of a temperature sensor disposed at the lower part of the mixing chamber, a stirring rod, and a cooling base; the stirring rod is configured to stir a solution to be mixed; the cooling base is at the bottom of the premixing chamber, the temperature sensor is connected to the central control system, and the central control system controls the cooling base to control the temperature in the mixing chamber;

the storage chamber is configured to store a prepared solution, and a drainage hose in communication with the conduit is disposed on the storage chamber;

the online real-time monitoring device consists of a plurality of sensors mounted in the mixing chamber and the storage chamber, and is configured to monitor various parameters of the prepared solution, and transmit data to the central control system to retain historical data in time.

Further, the stirring rod consists of a hollow main rod and a plurality of spiral slices mounted at the bottom of the main rod; the main rod is provided with an injection hole of ethanol solution, each of the spiral slices and the side wall of the main rod form a hollow structure having a triangular cross section, and a plurality of small holes are uniformly distributed on the side walls of the spiral slices; the interior of the hollow main rod communicates with the interiors of the spiral slices.

In order to prevent rhodamine B powder from being adsorbed on the screw and the spiral slices, and in view of the characteristic that rhodamine B is easily dissolved in ethanol, a small amount of ethanol solution is injected in the solution preparation process along the hole at the upper part of the main rod, and the ethanol flows in along the hole at the upper part of the main rod and flows out along the small holes of the spiral slices to take out the rhodamine B powder adsorbed on the spiral slices, thus ensuring the finish of the screw and improving the solution preparation rate.

Further, the water supply device consists of a water tank, an electric pump and an electric flow regulator, and is used for providing a stable water source; the electric pump provides power to continuously pump water in the water tank to the mixing chamber; the electric flow regulator controls the flow and inlet flow rate according to a signal sent by the central control system, and transmits the flow information to the central control system.

Further, a temperature sensor is provided in the mixing chamber, and the temperature sensor is disposed at the lower part of the mixing chamber. When premixing, the weight of dry powder and the water volume required are calculated according to the designed concentration and dosage, the electric flow regulator and an pressure regulating device are turned on successively, and the dry tracer powder and water are added into the mixing chamber. When the tracer is poured into the mixing chamber according to the dosage required by the designed concentration, the weight of the added tracer or the flow of the water is measured through the pressure regulating device and the electric flow regulator, and an adding continuing or adding stopping signal is sent to the central control system. Subsequently, the rotating speed and rotating time of the stirring screw are set through the central control system, and the tracer is rapidly stirred to prevent agglomeration. The cooling base is at the bottom of the premixing chamber, is combined with the temperature sensor to control the temperature of the premixing system, and is provided therein with an ice-water circulation conduit which can keep the temperature in the premixing chamber between 5° C. and 15° C. to prevent degradation of the tracer due to too high temperature. When the temperature rises, the central controller receives a signal from the temperature sensor, and sends an instruction to the ice-water circulation conduit to start operating; when the temperature is low, the ice-water circulation conduit stops operating.

Further, the online real-time monitoring device consists of an online tracer monitor, a turbidity sensor, a PH sensor, a corrosion rate monitor, a photoelectric liquid level sensor and a temperature sensor; during adding, the online real-time monitoring device monitors important water quality parameters in real time by using online sensors, and transmits the parameters to the central control system to retain historical data in time; the turbidity sensor, the PH sensor and the corrosion rate monitor are arranged in the mixing chamber and the storage chamber to monitor the turbidity, PH value and corrosion rate in the preparation and storage process of the tracer solution; the online tracer monitor is mounted in the mixing chamber to monitor the tracer concentration in the mixing chamber in real time; when the concentration of an agent is insufficient, the chemical agent can be supplemented to a designed concentration in time to ensure that the chemical agent in the system is always maintained in an optimal state;

the photoelectric liquid level sensor is mounted in the storage chamber to monitor the liquid level in real time; when the solution in the storage chamber is at a low liquid level, the sensor transmits a liquid level output signal to an adding control module of the central control system, and the device is started to carry out the process of solution preparation again; when the solution in the storage chamber is at a high liquid level, the sensor also sends a signal to stop the preparation of the solution.

Further, the inner walls of the premixing chamber, the mixing chamber and the storage chamber are uniformly coated with a black opaque paint.

Further, storage partitions are arranged on four sides of the upper part of the premixing chamber, the premixing chamber is filled with a drying agent and iron powder, and the iron powder is oxidized to absorb oxygen so as to provide a dry and light-proof environment for storing the tracer.

Further, an pressure regulating device is disposed at the upper part of the premixing chamber, the pressure regulating device regulates the pressure in the premixing chamber, a feeding pipe is disposed in the premixing chamber, one end of the feeding pipe is inserted into the tracer in the premixing chamber and the other end communicates with the mixing chamber; during the experiment, the premixing chamber is pressurized by the pressure regulating device, and the dry tracer powder enters the mixing chamber through the feeding pipe under the action of pressure.

Further, an pressure regulating device is disposed at the upper part of the mixing chamber, the pressure regulating device regulates the pressure in the mixing chamber, a feeding pipe is disposed in the mixing chamber, one end of the feeding pipe is inserted into the mixed solution in the mixing chamber and the other end communicates with the storage chamber; during the experiment, the dry tracer powder and water are mixed uniformly in the mixing chamber and prepared into a solution of a designed concentration; the mixing chamber is pressurized by the pressure regulating device, the solution enters the storage chamber through the feeding pipe under the action of pressure, and after the central control system sends an adding instruction, a certain amount of the solution is delivered by a metering pump to a specified point through the drainage hose.

Further, the real-time wireless monitoring system of fluorescent tracer mainly consists of a hydraulic self-charging power source, a multifunctional tracer monitoring probe, and a wireless ultrasonic flowmeter;

the hydraulic self-charging power source consists of a vortex charging device and a lithium battery which are connected by a wire; the vortex charging device is disposed in a drainage channel near a water outlet of a simulated conduit, the water flow drives a turbine to rotate, and a small generator disposed in the vortex charging device can convert mechanical energy into electrical energy and store the electrical energy in the lithium battery;

the multifunctional tracer monitoring probe is disposed on the model conduit, and can monitor the flow rate, water level, turbidity, conductivity and fluorescent tracer concentration, and transmit data to the central controller wirelessly;

the wireless ultrasonic flowmeter consists of a clamping sensor, a coupling agent and a connecting line; the coupling agent is smeared to the surface of the conduit, and the clamping sensor is clamped on the conduit to connect the central control system.

Further, the central control system consists of a central processing unit and a display screen; the central processing unit consists of a data storage module, a processing analysis module and a centralized control module; the data storage module is used for recording and storing tracer concentration, flow rate, and shot photos and images; the processing analysis module calculates and corrects the dynamic flow and the tracer recovery rate by using the collected data and images; the centralized control module consists of an adding control module and a collection control module for controlling the full-automatic control system for tracer adding and the real-time wireless monitoring system of fluorescent tracer respectively.

Using the device to simulate a real karst underground medium environment and inverting a karst underground medium structure by means of a tracer technology, including the following steps:

1) A current meter, a dosing system, a tracing instrument and the like are placed and assembled before a laboratory experiment starts.

2) A water inlet/outlet conduit is fully injected with water through a water supply system, a drain valve is opened to keep continuous water injection, and whether water leaks is checked. If water leaks, the water in the device is emptied, the water leakage position is plugged, and this step is repeated till no water leaks. After the conduit is full of water, further check is carried out to ensure no bubble residue in the conduit for the experiment.

3) Before the formal experiment, a tracer is used to carry out a uniform field simulation experiment under the same condition, a background value of a tap water tracer is measured, and the experimental time is estimated and mastered.

4) The experiment is started, the tracer is injected into the conduit once or continuously through the dosing system, real-time monitoring, recording and processing are carried out by the tracing instrument and a computer, and an inlet valve is closed when the monitored tracer concentration is negligible to end this experiment.

5) After this experiment, an outlet valve is completely opened, the entire device is flushed with tap water for about 10 min, and relevant experimental appliances are cleaned for next experiment. A complete experiment is finished through the above steps. Conduits of different combinations are changed, different flow rates are controlled to change the hydraulic condition, and steps 1) to 4) are repeated to obtain multiple groups of breakthrough curve of tracer concentrations. These curves and data are stored by the central processing unit, and learned and memorized by an artificial intelligence algorithm such as a neural network.

6) In an actual project, the water supply system, the tracer adding control system, the real-time wireless monitoring system of fluorescent tracer and the central control system of the present invention may be applied to a field tracer experiment. The water supply system and the tracer adding control system are placed at an adding point (such as a drill hole, a river, or a ponor), the tracer is added at a fixed point, the real-time wireless monitoring system of fluorescent tracer is mounted at an outlet (such as the low course of a river, or a ponor), and data and breakthrough curve of tracer concentrations are recorded in real time by the central control system.

7) Finally, the curves and data obtained from the field experiment are input to the artificial intelligence algorithm by the central processing unit, and analyzed by contrasting with laboratory experiment results to realize speculation of underground karst medium structures and inversion of relevant structure parameters.

The present invention studies a laboratory tracer experiment system based on karst conduit medium characteristic inversion and an operating method, solves the technical problems that no relatively systematic laboratory tracer exploration experiment has been carried out in previous studies and there's a lack of devices and methods related to tracer technology analysis for karst conduit media. Compared with the previous studies, the device of the present invention has the following advantages:

1) Solute transport tracer simulation can be carried out on multiple combined karst conduit models, the karst underground medium environment can be truly restored to a large extent by using various different combining forms such as straight conduits, underground puddles and hydraulic drops and changing the flow rate and the cross-sectional size and length of the conduits, and the karst conduit models used can be assembled and disassembled for reuse, and are visible due to the use of a high-strength PVC transparent material.

2) The heights of threaded lifting pipes can be adjusted to carry out multiple laboratory tracer experiments of different water head differences so as to stimulate the water head differences in real karst environments.

3) Single adding, multiple times of intermittent adding and pulsed adding of the tracer can be achieved by programming. Tracer powder is continuously prepared and added, so the entire process of preparing the powder into a solution is full-automatic, safe and continuous.

4) The real-time wireless monitoring system of fluorescent tracer is used to monitor the concentration of the fluorescent tracer and the flow rate in real time and transmit the data remotely and wirelessly, and an uninterrupted self-powered function is realized by hydroelectric power generation, so that an unattended laboratory experiment can be implemented.

5) A high-definition camera is used to record and shoot the whole transport process of the fluorescent tracer in the conduit, and a display screen is used for real-time visual display.

BRIEF DESCRIPTIONS OF THE DRAWINGS

The accompanying drawings constituting a part of the present application are intended to provide a further understanding of the present application, and the illustrative embodiments of the present application and the descriptions thereof are intended to interpret the present application and do not constitute improper limitations to the present application.

FIG. 1 is an overall structure diagram according to the present invention.

In which: 1, conduit model; 2, O-shaped seal ring; 3, test base; 4, drainage channel; 5, slide rail; 6, height adjustable support frame (consisting of 6a, threaded lifting pipe; 6b, splicing collar); 7, water storage tank; 8, water pump; 9, water pressure regulator and pressure instrument; 10, matched pipe; 11, tracer adding control device and water tank; 12, hydraulic self-charging lithium battery; 13, vortex charging device; 14, multifunctional tracer monitoring probe; 15, wireless ultrasonic flowmeter; 16, central processing unit; 17, display screen; 18, high-definition camera; A, single straight conduit model; B, branched conduit model; C, pool conduit model; D, drop conduit model;

11-1, water tank; 11-2, electric pump; 11-3, electric flow regulator; 11-4, premixing chamber; 11-5, mixing chamber; 11-6, storage chamber; 11-7, dry tracer powder; 11-8, stirring screw, 8a, main rod; 8b, spiral slice; 11-9, online tracer monitor; 11-10, photoelectric liquid level sensor; 11-11, various online sensors; 12, metering pump; 11-13, drainage hose; 11-14, air pressure regulating valve; 11-15, cooling base; 11-16, feeding pipe; 11-18, electronic weighing system.

DETAILED DESCRIPTION OF THE EMBODIMENTS

It should be noted that the following detailed descriptions are exemplary and are intended to provide further descriptions of the present application. All technical and scientific terms used herein have the same meaning as commonly understood by those of ordinary skill in the technical filed to which the present application belongs, unless otherwise indicated.

It should be noted that the terms used here are merely used for describing specific embodiments, but are not intended to limit the exemplary embodiments of the present invention. As used herein, unless otherwise clearly stated in the context, singular forms are also intended to include plural forms. In addition, it should also be understood that when the terms "comprise" and/or "include" are used in the description, it indicates the presence of features, steps, operations, devices, components, and/or combinations thereof.

As described in Background of the Invention, there are deficiencies in the prior art. In order to solve the above technical problems, the present application proposes a laboratory tracer experiment system based on karst conduit medium characteristic inversion to solve the technical problems that no relatively systematic laboratory tracer exploration experiment has been carried out in previous studies and there's a lack of devices and methods related to of tracer technology analysis for karst conduit media.

Figure 1:
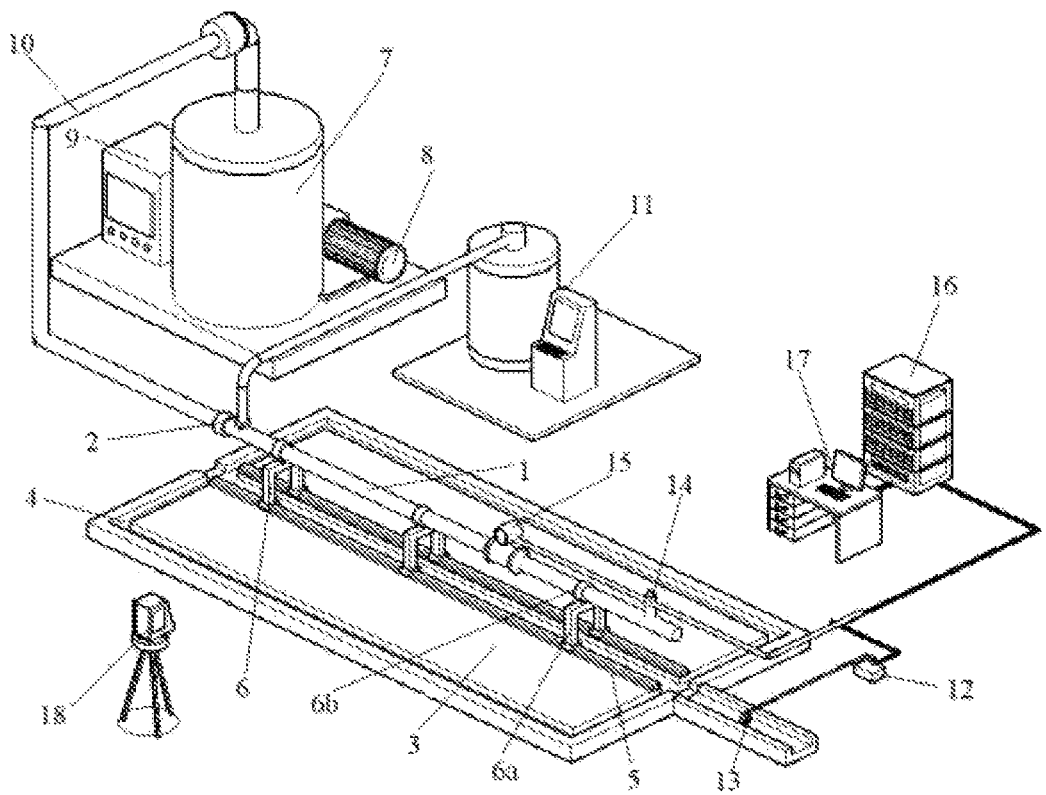
Figure 2:
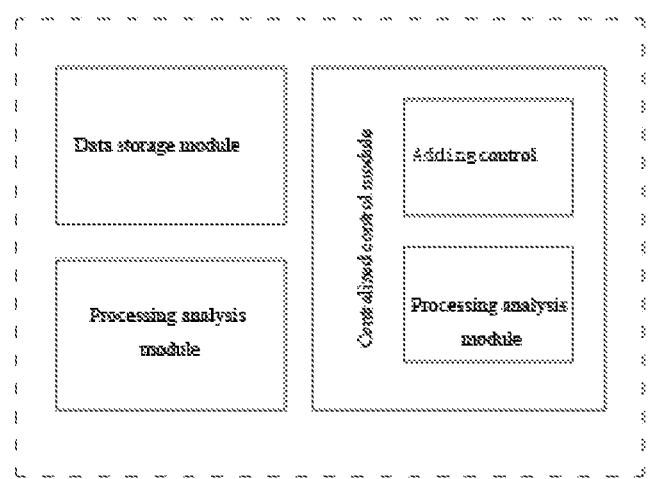
FIG. 2 is a modular structure diagram of a central processing unit according to the present invention.
Figure 3:
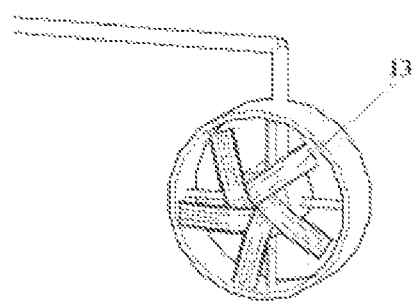
FIG. 3 is a detailed diagram of a vortex charging device.

In a typical embodiment of the present application, as shown in FIG. 1, a laboratory tracer experiment system based on karst conduit medium characteristic inversion consists of a assembly model system of the karst conduit medium, a test bed, a water supply system, a full-automatic control system for tracer adding, a real-time wireless monitoring system of fluorescent tracer, a central control system and a high-definition camera recording system.

A karst conduit medium assembly model and the test bed are main experimental places, a plurality of assembly conduit models is combined to simulate different types of underground karst media, flow rate measurement and tracer adding are carried out at an inlet, and real-time data acquisition and monitoring are carried out at an outlet to obtain tracer curve characteristics of different karst medium structures.

The assembly model system of the karst conduit medium consists of a series of conceptual model of karst conduits of design sizes and types. The conceptual model of karst conduits designed and combined according to certain rule can be conveniently assembled, disassembled and reused.

Figure 4:
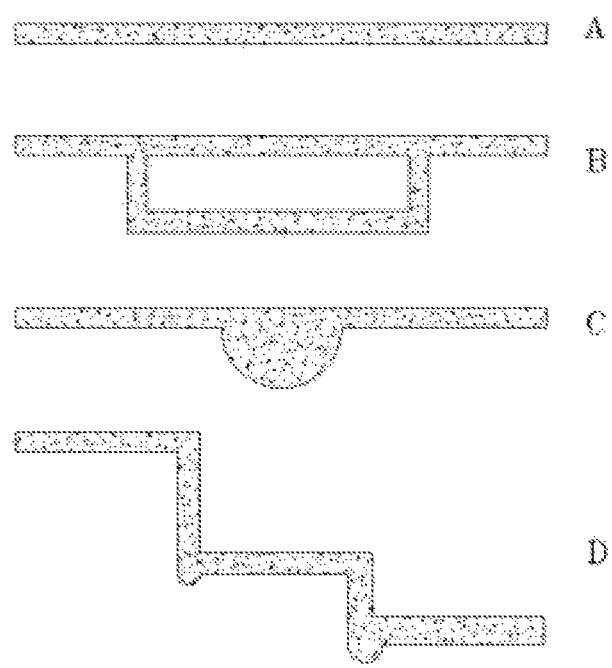
FIG. 4 shows four types of basic conduit models.

The conduit model is made of a hard high-strength PVC transparent material, and can be used for visually observing the change in tracer concentration during a tracer experiment. An opening connected to the tracer adding control system and an opening connected to the real-time wireless monitoring system of fluorescent tracer are respectively disposed at positions of the conduit near the inlet and the outlet, and the openings are sealed by O-shaped seal rings to prevent leakage of liquid during the experiment. According to the common types of underground karst conduits in the southwest of China, the characteristics thereof are summarized to design four major types of basic conduit models including single straight conduit models, branched conduit models, pool conduit models and drop conduit models. Specifically, FIG. 4 shows four types of conduit models, i.e., single straight conduit model A, branched conduit model B, pool conduit model C, and drop conduit model D.

As shown in FIG. 1, the test bed and the water supply system include a bed base and a water supply device.

The bed base 2 of the test bed is 20 cm thick, 12 m long and 4 m wide and is cast by concrete. 15 cm drainage channels are disposed in the middle of and on four sides of the bed base to discharge excess water in the experiment to sewers. The entire test bed is placed on a concrete platform to facilitate assembly and disassembly. Two slide rails are disposed on two sides of the middle drainage channel, and a plurality of height adjustable support frames is loaded on the slide rails for placing the assembly conduit experimental model and loading a dosing device and a tracing instrument.

The height adjustable support frame 6 is made of a high-strength ABS material, consists of a refitted ABS threaded lifting pipe 6a and a splicing collar 6b, and is used for fixing the model conduit. During the experiment, the height adjustable support frames are fixed on the slide rails 5. By adjusting the heights of the threaded lifting pipes, tracer experiments of different head differences can be carried out to stimulate true height differences. The model conduit can be conveniently replaced by sliding the height adjustable support frames.

As shown in FIG. 1, the water supply device consists of a water storage tank 7, a water pump 8, a water pressure regulator and pressure instrument 9, a matched pipe 10, etc., the water pump provides a required water pressure, and the water storage tank can provide a constant water source to realize stable water supply.

Figure 5:
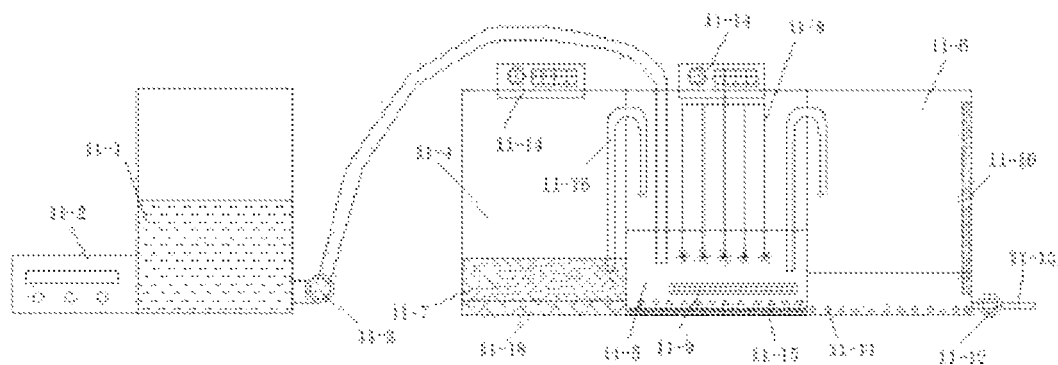
FIG. 5 is a structure diagram of a full-automatic control system for tracer adding.

As shown in FIG. 5, the full-automatic control system for tracer adding continuously prepares and adds tracer powder, so the entire process of preparing the powder into a solution is full-automatic, safe and continuous. The concentration of the solution can be fully automatically, accurately and continuously controlled, and the volume of the solution added is strictly controlled. The adding method may be single adding, multiple times of adding or pulsed adding according to programming, so the efficiency is high, and the labor cost of tracer adding is greatly saved. An integrated three-chamber-combined device is adopted, and three chambers can operate at the same time to continuously prepare the tracer solution efficiently and conveniently. To meet the requirements for long-term preparation and storage of the fluorescent tracer rhodamine B, in consideration of its properties of easy photolysis and oxidation and strong adsorption, the device is further provided with a cooling base, a special stirring screw and the like to reduce the adsorption in the dissolution process, and a low-temperature shading preparation and storage environment is provided for the tracer.

The present invention can monitor and collect information such as liquid level, concentration, turbidity, PH value and corrosion rate during the preparation and adding process of the tracer, comprehensively monitor the preparation and adding process, control the whole process more accurately and efficiently with strong comprehensiveness, and improve the experimental efficiency. The specific structure is as follows:

The full-automatic control system for tracer adding consists of a water supply device, an integrated three-chamber-combined device, a central control system and an online real-time monitoring device;

The integrated three-chamber-combined device consists of a premixing chamber, a mixing chamber and a storage chamber which are sequentially connected;

The premixing chamber 11-4 is used for storing three kinds of dry tracer powder 11-7, i.e., rhodamine, fluorescein sodium and Tinopal, a weighing device is disposed at the bottom of the premixing chamber, and the weighing device is configured to detect the weight of the dry tracer powder and send detected signals to the central control system; the central control system controls the weight of the dry tracer powder entering the mixing chamber;

The mixing chamber 11-5 is used for preparation of a tracer solvent, and the water supply device supplies water to the mixing chamber; the mixing chamber consists of a temperature sensor disposed at the lower part of the mixing chamber, a stirring rod, and a cooling base 11-15; the stirring rod is configured to stir a solution to be mixed; the cooling base is at the bottom of the premixing chamber, the temperature sensor is connected to the central control system, and the central control system controls the cooling base to control the temperature in the mixing chamber;

The storage chamber 11-6 is configured to store a prepared solution, and a drainage hose 11-13 in communication with the conduit is disposed on the storage chamber.

The online real-time monitoring device consists of a plurality of sensors mounted in the mixing chamber and the storage chamber, and is configured to monitor various parameters of the prepared solution, and transmit data to the central control system to retain historical data in time.

Figure 6:
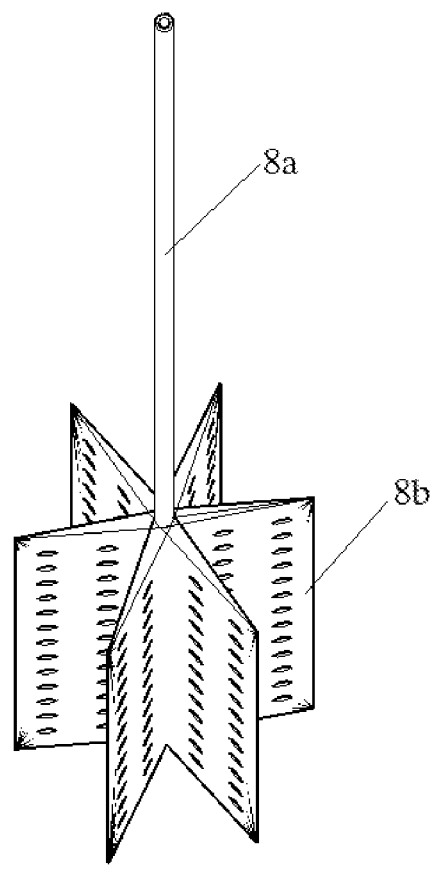
FIG. 6 is a structure diagram of a stirring rod.

As shown in FIG. 6, the stirring rod consists of a hollow main rod 8*a* and a plurality of spiral slices 8*b* mounted at the bottom of the main rod. The main rod is provided with an injection hole of ethanol solution, each of the spiral slices is of a hollow structure having a triangular cross section, and a plurality of controllable small holes are uniformly distributed on the spiral slices; the interior of the hollow main rod communicates with the interiors of the spiral slices. In order to prevent rhodamine B powder from being adsorbed on the screw and the spiral slices, and in view of the characteristic that rhodamine B is easily dissolved in ethanol, a small amount of ethanol solution is injected in the solution preparation process along the hole at the upper part of the main rod, and the ethanol flows in along the hole at the upper part of the main rod and flows out along the small holes of the spiral slices to take out the rhodamine B powder adsorbed on the spiral slices, thus ensuring the finish of the screw and improving the solution preparation rate.

Further, the water supply device consists of a water tank 11-1, an electric pump 11-2 and an electric flow regulator 11-3, and is used for providing a stable water source; the electric pump provides power to continuously pump water in the water tank to the mixing chamber; the electric flow regulator controls the flow and inlet flow rate according to a signal sent by the central control system, and transmits the flow information to the central control system.

Further, a temperature sensor is provided in the mixing chamber, and the temperature sensor is disposed at the lower part of the mixing chamber. When premixing, the weight of dry powder and the water volume required are calculated according to the designed concentration and dosage, the electric flow regulator and an pressure regulating device are turned on successively, and the dry tracer powder and water are added into the mixing chamber. When the tracer is poured into the mixing chamber according to the dosage required by the designed concentration, the weight of the added tracer or the flow of the water is measured through the pressure regulating device and the electric flow regulator, and an adding continuing or adding stopping signal is sent to the central control system. Subsequently, the rotating speed and rotating time of the stirring screw are set through the central control system, and the tracer is rapidly stirred to prevent agglomeration. The cooling base is at the bottom of the premixing chamber, is combined with the temperature sensor to control the temperature of the premixing system, and is provided therein with an ice-water circulation conduit which can keep the temperature in the premixing chamber between 5° C. and 15° C. to prevent degradation of the tracer due to too high temperature. When the temperature rises, the central controller receives a signal from the temperature sensor, and sends an instruction to the ice-water circulation conduit to start operating; when the temperature is low, the ice-water circulation conduit stops operating.

Further, the online real-time monitoring device consists of an online tracer monitor 11-9, a turbidity sensor, a PH sensor, a corrosion rate monitor, a photoelectric liquid level sensor 11-10 and a temperature sensor; during adding, the online real-time monitoring device monitors important water quality parameters in real time by using online sensors, and transmits the parameters to the central control system to retain historical data in time. The turbidity sensor, the PH sensor and the corrosion rate monitor are arranged in the mixing chamber and the storage chamber to monitor the turbidity, PH value and corrosion rate in the preparation and storage process of the tracer solution.

The online tracer monitor is mounted in the mixing chamber to monitor the tracer concentration in the mixing chamber in real time. When the concentration of an agent is insufficient, the chemical agent can be supplemented to a designed concentration in time to ensure that the chemical agent in the system is always maintained in an optimal state.

The photoelectric liquid level sensor is mounted in the storage chamber to monitor the liquid level in real time; when the solution in the storage chamber is at a low liquid level, the sensor transmits a liquid level output signal to an adding control module of the central control system, and the device is started to carry out the process of solution preparation again; when the solution in the storage chamber is at a high liquid level, the sensor also sends a signal to stop the preparation of the solution.

Further, the inner walls of the premixing chamber, the mixing chamber and the storage chamber are uniformly coated with a black opaque paint. Storage partitions are arranged on four sides of the upper part of the premixing chamber, the premixing chamber is filled with a drying agent and iron powder, and the iron powder is oxidized to absorb oxygen so as to provide a dry and light-proof environment for storing the tracer.

Further, an pressure regulating device 11-14 is disposed at the upper part of the premixing chamber, the pressure regulating device regulates the pressure in the premixing chamber, a feeding pipe is disposed in the premixing chamber, one end of the feeding pipe is inserted into the tracer in the premixing chamber and the other end communicates with the mixing chamber; during the experiment, the premixing chamber is pressurized by the pressure regulating device, and the dry tracer powder enters the mixing chamber through the feeding pipe under the action of pressure.

Further, an pressure regulating device 11-14 is disposed at the upper part of the mixing chamber, the pressure regulating device regulates the pressure in the mixing chamber, a feeding pipe 11-16 is disposed in the mixing chamber, one end of the feeding pipe 11-16 is inserted into the mixed solution in the mixing chamber and the other end communicates with the storage chamber; during the experiment, the dry tracer powder and water are mixed uniformly in the mixing chamber and prepared into a solution of a designed concentration; the mixing chamber is pressurized by the pressure regulating device, the solution enters the storage chamber through the feeding pipe under the action of pressure, and after the central control system sends an adding instruction, a certain amount of the solution is delivered by a metering pump to a specified point through the drainage hose.

The real-time wireless monitoring system of fluorescent tracer mainly consists of a hydraulic self-charging power source, a multifunctional tracer monitoring probe, and a wireless ultrasonic flowmeter, monitors the concentration of the fluorescent tracer and the flow rate in real time, and realizes a remote wireless transmission function of data, so that the system can be used under unattended conditions.

The hydraulic self-charging power source consists of a vortex charging device and a lithium battery which are connected by a wire. During a tracer experiment, the vortex charging device is thrown into a drainage channel near a water inlet/outlet, the water flow drives a turbine to rotate, and a small generator disposed in the vortex charging device can convert mechanical energy into electrical energy and store the electrical energy in the lithium battery. The hydraulic self-charging power source is used for supplying power to the multifunctional tracer monitoring probe and the wireless ultrasonic flowmeter.

The multifunctional tracer monitoring probe can monitor the flow rate, water level, turbidity, conductivity and fluorescent tracer concentration, and transmit data to the central controller wirelessly.

The wireless ultrasonic flowmeter consists of a clamping sensor, a coupling agent and a connecting line. During the experiment, the coupling agent is smeared to the surface of the conduit, the sensor is clamped on the conduit, and the host is connected for measurement. The wireless ultrasonic flowmeter avoids the conventional conduit breaking operation, saves more time and labor, and ensures the tightness of the conduit. The clamping sensor can match a conduit having a diameter of 15 mm-6000 mm, with a measurement accuracy of 0.1 m/s.

The central controller consists of a central processing unit and a display screen, and includes a data storage module, a processing analysis module and a centralized control module. The data storage module is used for recording and storing tracer concentration, flow rate, and shot photos and images. The processing analysis module calculates and corrects the dynamic flow and the tracer recovery rate by using the collected data and images. The centralized control module consists of an adding control module and a collection control module for controlling the full-automatic control system for tracer adding and the real-time wireless monitoring system of fluorescent tracer respectively. Specifically, the adding control module can carry out programming input according to experimental needs, and can achieve three effects of single adding, multiple times of intermittent adding, and pulsed adding. The display screen displays the concentration, flow rate and images in real time.

The high-definition camera recording system can record and shoot the whole transport process of the fluorescent tracer in the conduit, and transmit the images and videos to the central processing unit in real time wirelessly. The images and videos and the collected tracer concentration and flow rate are visually displayed on the display screen to provide basis and help for processing and analyzing late data.

Using the device to simulate a real karst underground medium environment and inverting a karst underground medium structure by means of a tracer technology, including the following steps:

1) A current meter, a dosing system, a tracing instrument and the like are placed and assembled before a laboratory experiment starts.

2) A water inlet/outlet conduit is fully injected with water through a water supply system, a drain valve is opened to keep continuous water injection, and whether water leaks is checked. If water leaks, the water in the device is emptied, the water leakage position is plugged, and this step is repeated till no water leaks. After the conduit is full of water, further check is carried out to ensure no bubble residue in the conduit for the experiment.

3) Before the formal experiment, a tracer is used to carry out a uniform field simulation experiment under the same condition, a background value of a tap water tracer is measured, and the experimental time is estimated and mastered.

4) The experiment is started, the tracer is injected into the conduit once or continuously through the dosing system, real-time monitoring, recording and processing are carried out by the tracing instrument and a computer, and an inlet valve is closed when the monitored tracer concentration is negligible to end this experiment.

5) After this experiment, an outlet valve is completely opened, the entire device is flushed with tap water for about 10 min, and relevant experimental appliances are cleaned for next experiment. A complete experiment is finished through the above steps. Conduits of different combinations are changed, different flow rates are controlled to change the hydraulic condition, and steps 1) to 4) are repeated to obtain multiple groups of breakthrough curve of tracer concentrations. These curves and data are stored by the central processing unit, and learned and memorized by an artificial intelligence algorithm such as a neural network.

6) In an actual project, the water supply system, the tracer adding control system, the real-time wireless monitoring system of fluorescent tracer and the central control system of the present invention may be applied to a field tracer experiment. The water supply system and the tracer adding control system are placed at an adding point (such as a drill hole, a river, or a ponor), the tracer is added at a fixed point, the real-time wireless monitoring system of fluorescent tracer is mounted at an outlet (such as the low course of a river, or a ponor), and data and breakthrough curve of tracer concentrations are recorded in real time by the central control system.

7) Finally, the curves and data obtained from the field experiment are input to the artificial intelligence algorithm by the central processing unit, and analyzed by contrasting with laboratory experiment results to realize speculation of underground karst medium structures and inversion of relevant structure parameters.

Compared with the previous studies, the device of the present invention has the following advantages:

Solute transport tracer simulation can be carried out on multiple combined karst conduit models, the karst underground medium environment can be truly restored to a large extent by using various different combining forms such as straight conduits, underground puddles and hydraulic drops and changing the flow rate and the cross-sectional size and length of the conduits, and the karst conduit models used can be assembled and disassembled for reuse, and are visible due to the use of a high-strength PVC transparent material.

The heights of threaded lifting pipes can be adjusted to carry out multiple laboratory tracer experiments of different water head differences so as to stimulate the water head differences in real karst environments.

Single adding, multiple times of intermittent adding and pulsed adding of the tracer can be achieved by programming. Tracer powder is continuously prepared and added, so the entire process of preparing the powder into a solution is full-automatic, safe and continuous.

The real-time wireless monitoring system of fluorescent tracer is used to monitor the concentration of the fluorescent tracer and the flow rate in real time and transmit the data remotely and wirelessly, and an uninterrupted self-powered function is realized by hydroelectric power generation, so that an unattended laboratory experiment can be implemented.

A high-definition camera is used to record and shoot the whole transport process of the fluorescent tracer in the conduit, and a display screen is used for real-time visual display.

The above descriptions are only the preferred embodiments of the present application, and are not intended to limit the present application. Various changes and variations may be made to the present application by those skilled in the art. Any modifications, equivalent substitutions, improvements and the like made within the spirit and principle of the present application shall fall within the scope of the present application.

The invention claimed is:

1. A laboratory tracer experiment system based on karst conduit medium characteristic inversion, comprising:
a assembly model system of the karst conduit medium, a test bed, a water supply system, a full-automatic control system for tracer adding, a real-time wireless monitoring system of fluorescent tracer, a central control system and a high-definition camera recording system;
the assembly model system of the karst conduit medium consists of a series of conceptual model of karst conduits of designed sizes and types, and is configured to simulate different types of underground karst media;
flow rate measurement and tracer adding are carried out at an inlet of each conduit, and real-time data acquisition and monitoring are carried out at an outlet to obtain tracer curve characteristics of different karst medium structures;
the test bed is configured to support the assembly model system of the karst conduit medium; the water supply system is connected to the assembly model system of the karst conduit medium to supply water to the assembly model system of the karst conduit medium;
the full-automatic control system for tracer adding is connected to the assembly model system of the karst conduit medium to add a prepared tracer solution into the assembly model system of the karst conduit medium;
the real-time wireless monitoring system of fluorescent tracer is configured to monitor the concentration of a fluorescent tracer and the flow rate in real time, and implement remote wireless transmission of data;
the high-definition camera recording system is configured to record and shoot the whole transport process of the fluorescent tracer in the conduit, and transmit images and videos in real time to the central control system wirelessly, and the images and videos and the collected tracer concentration and flow rate are visually displayed on the display screen to provide basis and help for processing and analyzing late data;
the central control system controls the full-automatic control system for tracer adding, the water supply system, the real-time wireless monitoring system of fluorescent tracer and the high-definition camera recording system to communicate with the central control system.

2. The laboratory tracer experiment system based on karst conduit medium characteristic inversion according to claim 1, wherein the conduit model is made of a transparent material; an opening connected to the full-automatic control system for tracer adding is disposed at a position of the conduit model near the inlet, an opening connected to the real-time wireless monitoring system of fluorescent tracer is disposed near the outlet, and the two openings are sealed by seal rings.

3. The laboratory tracer experiment system based on karst conduit medium characteristic inversion according to claim 1, wherein the test bed comprises a bed base and support frames, and drainage channels are disposed in the middle of and on four sides of the bed base; two slide rails are disposed on two sides of the middle drainage channel, a plurality of height adjustable support frames is mounted on the two slide rails, and the assembly model system of the karst conduit medium is mounted on the support frames.

4. The laboratory tracer experiment system based on karst conduit medium characteristic inversion according to claim 1, wherein the full-automatic control system for tracer adding comprises a water supply device, an integrated three-chamber-combined device, a central control system and an online real-time monitoring device;
the integrated three-chamber-combined device comprises a premixing chamber, a mixing chamber and a storage chamber which are sequentially connected;
the premixing chamber is used for storing dry powder of three tracers, i.e., rhodamine, fluorescein sodium and Tinopal, a weighing device is disposed at the bottom of the premixing chamber, and the weighing device is configured to detect the weight of the dry tracer powder and send detected signals to the central control system; the central control system controls the weight of the dry tracer powder entering the mixing chamber;

the mixing chamber is used for preparation of a tracer solvent, and the water supply device supplies water to the mixing chamber; the mixing chamber comprises a temperature sensor disposed at the lower part of the mixing chamber, a stirring rod, and a cooling base; the stirring rod is configured to stir a solution to be mixed; the cooling base is at the bottom of the premixing chamber, the temperature sensor is connected to the central control system, and the central control system controls the cooling base to control the temperature in the mixing chamber;

the storage chamber is configured to store a prepared solution, and a drainage hose in communication with the conduit is disposed on the storage chamber;

the online real-time monitoring device comprises a plurality of sensors mounted in the mixing chamber and the storage chamber, and is configured to monitor various parameters of the prepared solution, and transmit data to the central control system to retain historical data in time.

5. The laboratory tracer experiment system based on karst conduit medium characteristic inversion according to claim 4, wherein the stirring rod comprises a hollow main rod and a plurality of spiral slices mounted at the bottom of the main rod; the main rod is provided with an injection hole of ethanol solution, each of the spiral slices and the side wall of the main rod form a hollow structure having a triangular cross section, and a plurality of small holes are uniformly distributed on the side walls of the spiral slices; the interior of the hollow main rod communicates with the interiors of the spiral slices.

6. The laboratory tracer experiment system based on karst conduit medium characteristic inversion according to claim 4, wherein the water supply device comprises a water tank, an electric pump and an electric flow regulator, and is used for providing a stable water source; the electric pump provides power to continuously pump water in the water tank to the mixing chamber; the electric flow regulator controls the flow and inlet flow rate according to a signal sent by the central control system, and transmits the flow information to the central control system.

7. The laboratory tracer experiment system based on karst conduit medium characteristic inversion according to claim 4, wherein the online real-time monitoring device comprises an online tracer monitor, a turbidity sensor, a PH sensor, a corrosion rate monitor, a photoelectric liquid level sensor and a temperature sensor; during adding, the online real-time monitoring device monitors important water quality parameters in real time by using online sensors, and transmits the parameters to the central control system to retain historical data in time; the turbidity sensor, the PH sensor and the corrosion rate monitor are arranged in the mixing chamber and the storage chamber to monitor the turbidity, PH value and corrosion rate in the preparation and storage process of the tracer solution;

the online tracer monitor is mounted in the mixing chamber to monitor the tracer concentration in the mixing chamber in real time; when the concentration of an agent is insufficient, the chemical agent can be supplemented to a designed concentration in time to ensure that the chemical agent in the system is always maintained in an optimal state;

the photoelectric liquid level sensor is mounted in the storage chamber to monitor the liquid level in real time; when the solution in the storage chamber is at a low liquid level, the sensor transmits a liquid level output signal to an adding control module of the central control system, and the device is started to carry out the process of solution preparation again; when the solution in the storage chamber is at a high liquid level, the sensor also sends a signal to stop the preparation of the solution.

8. The laboratory tracer experiment system based on karst conduit medium characteristic inversion according to claim 4, wherein an pressure regulating device is disposed at the upper part of the premixing chamber, the pressure regulating device regulates the pressure in the premixing chamber, a feeding pipe is disposed in the premixing chamber, one end of the feeding pipe is inserted into the tracer in the premixing chamber and the other end communicates with the mixing chamber; an pressure regulating device is disposed at the upper part of the mixing chamber, the pressure regulating device regulates the pressure in the mixing chamber, a feeding pipe is disposed in the mixing chamber, one end of the feeding pipe is inserted into the mixed solution in the mixing chamber and the other end communicates with the storage chamber.

9. The laboratory tracer experiment system based on karst conduit medium characteristic inversion according to claim 1, wherein the real-time wireless monitoring system of fluorescent tracer mainly comprises a hydraulic self-charging power source, a multifunctional tracer monitoring probe, and a wireless ultrasonic flowmeter;

the hydraulic self-charging power source consists of a vortex charging device and a lithium battery which are connected by a wire; the vortex charging device is disposed in a drainage channel near a water outlet of a simulated conduit, the water flow drives a turbine to rotate, and a small generator disposed in the vortex charging device can convert mechanical energy into electrical energy and store the electrical energy in the lithium battery;

the multifunctional tracer monitoring probe is disposed on the model conduit, and can monitor the flow rate, water level, turbidity, conductivity and fluorescent tracer concentration, and transmit data to the central controller wirelessly;

the wireless ultrasonic flowmeter comprises a clamping sensor, a coupling agent and a connecting line; the coupling agent is smeared to the surface of the conduit, and the clamping sensor is clamped on the conduit to connect the central control system.

10. The laboratory tracer experiment system based on karst conduit medium characteristic inversion according to claim 1, wherein the central control system consists of a central processing unit and a display screen; the central processing unit comprises a data storage module, a processing analysis module and a centralized control module; the data storage module is used for recording and storing tracer concentration, flow rate, and shot photos and images; the processing analysis module calculates and corrects the dynamic flow and the tracer recovery rate by using the collected data and images; the centralized control module consists of an adding control module and a collection control module for controlling the full-automatic control system for tracer adding and the real-time wireless monitoring system of fluorescent tracer respectively.

* * * * *